United States Patent [19]

Cosentino et al.

[11] 4,123,091
[45] Oct. 31, 1978

[54] TUBE CONNECTOR

[75] Inventors: Louis C. Cosentino, Wayzata; B. Steven Springrose, Minneapolis, both of Minn.

[73] Assignee: Renal Systems, Inc., Minneapolis, Minn.

[21] Appl. No.: 853,133

[22] Filed: Nov. 21, 1977

[51] Int. Cl.² .................. F16L 21/08; F16L 37/12
[52] U.S. Cl. .......................... 285/39; 128/214 R; 285/307; 285/319; 285/DIG. 22
[58] Field of Search .............. 285/319, 307, 38, 39, 285/DIG. 22

[56] References Cited

U.S. PATENT DOCUMENTS

| 517,192 | 3/1894 | Prior | 285/319 X |
|---|---|---|---|
| 1,904,061 | 4/1933 | Larson | 285/319 X |
| 2,550,591 | 4/1951 | Parsons | 285/319 |
| 3,394,954 | 7/1968 | Sarns | 285/423 X |
| 3,569,903 | 3/1971 | Brishka | 285/319 X |
| 3,588,149 | 6/1971 | Demler, Sr. | 285/307 X |
| 3,603,621 | 9/1971 | Parsons | 285/319 |
| 3,876,234 | 4/1975 | Harms | 285/38 |
| 3,986,508 | 10/1976 | Barrington | 285/3 X |

Primary Examiner—Thomas F. Callaghan
Attorney, Agent, or Firm—Irving S. Rappaport

[57] ABSTRACT

A flow-through or fluid coupling connector assembly possessing positive locking connect and ready disconnect comprising two connector bodies; one having a male tubular member, and the other having a female tubular member for receiving the male member upon connection of the two bodies together. The male tubular member of the one connector body has resilient arm members spaced from and extending along opposite sides of the tubular member's axis with the free remote ends of the arms flaring outwardly therefrom. The arm members are each provided with an inwardly projecting flange member for locking the two connector bodies together by fitting into a recessed collar on the other connector body. The other connector body has projections at opposite sides thereof which are of a size and spaced to bear outwardly against the arm members of the one connector body, the spacing being such that on rotation of one of the connector bodies relative to the other, the projections bear against the arms to spread them and lift the flanges out of the recessed collar for separation of the bodies.

9 Claims, 5 Drawing Figures

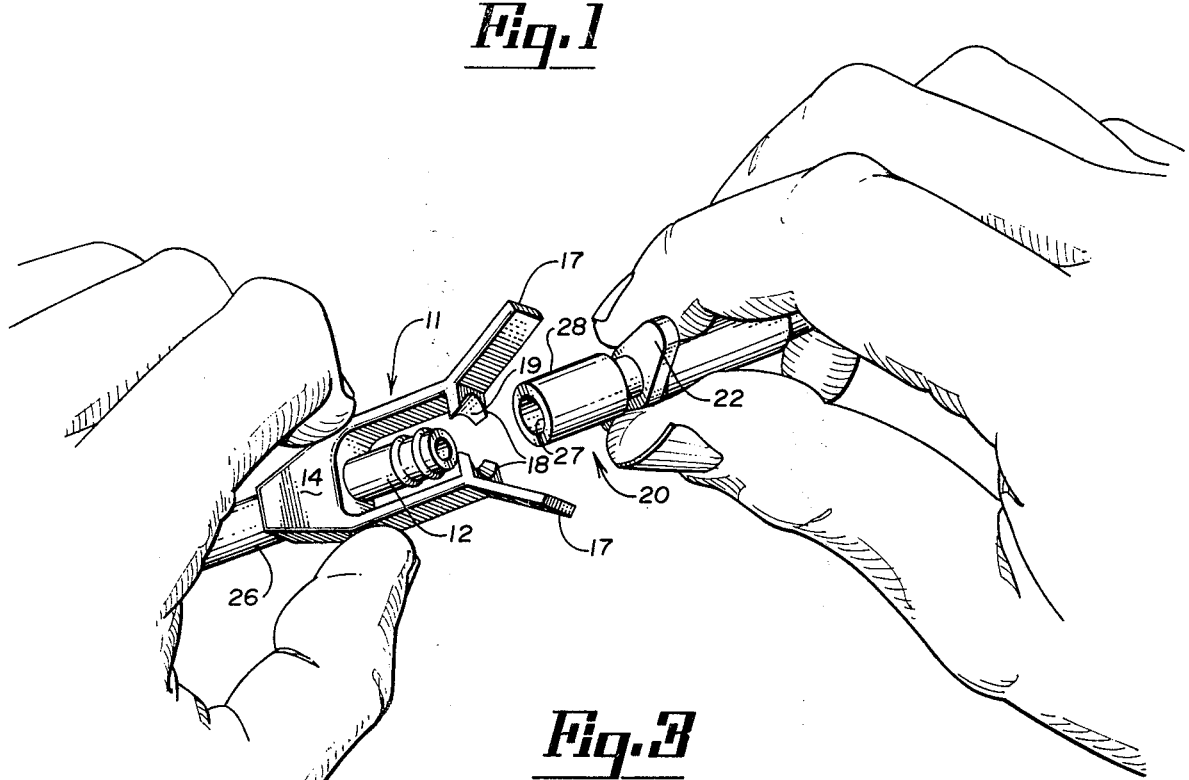
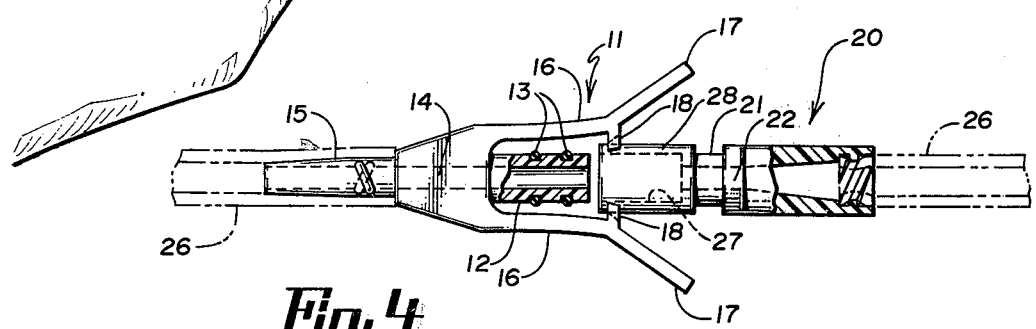
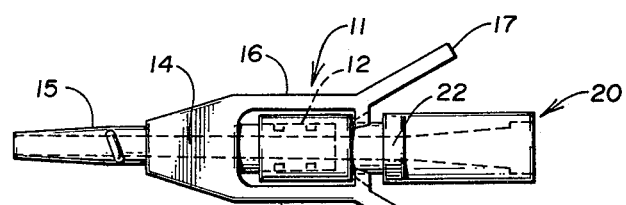
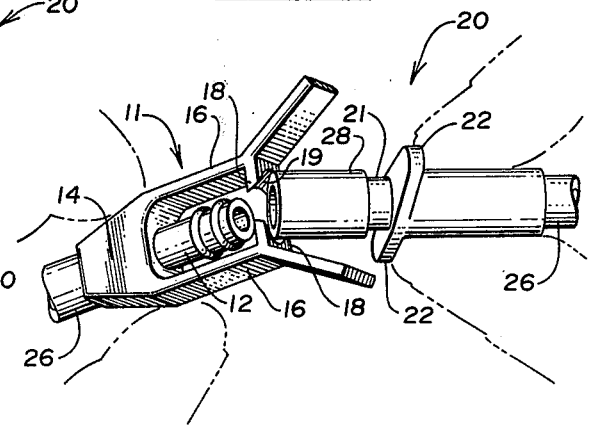
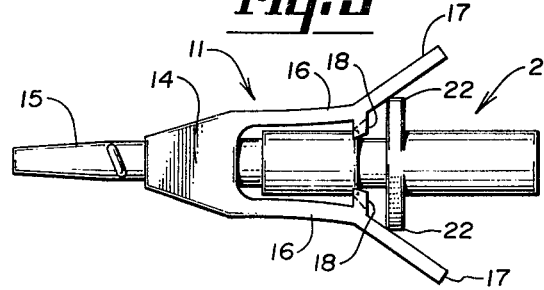

TUBE CONNECTOR

BACKGROUND OF THE INVENTION

In many tubing assemblies there is a need to have a male and female flow-through coupling assembly that can be readily joined in a locked relationship which is positive and leak proof. Latching and unlatching is desirably simple yet positive with a readily connectable and disconnectable arrangement.

The present invention provides such a structure that can be readily molded from various materials including transparent plastic materials and readily connected and disconnected. While the invention will be useful in many applications, it has been specifically designed for use with flexible plastic tubing for use in artificial kidney machines. The invention will be readily understood by reference to the specification and drawings.

THE DRAWINGS

FIG. 1 is a perspective view of the connector assembly of the invention in disconnected and spaced arrangement;

FIG. 2 is a perspective view of the connector bodies as they are being engaged to be connected;

FIG. 3 is a side elevational view of the connector bodies partially joined and shows the connection of the connector bodies to remote ends of lengths of tubing for transmitting fluid flow therethrough;

FIG. 4 is a side elevational view of joined connector bodies with the flanges latched in a lock position into the recessed colar;

FIG. 5 is a side elevation view of the joined connector bodies with the outward projections of the one connector body rotated to spread the arms and latch members of the other connector body thereby permitting disconnect of the connector bodies.

DESCRIPTION OF THE PREFERRED EMBODIMENT

FIG. 1 is a perspective view of a connector coupling in accordance with the invention. Typically, the coupling will be formed of an inert thermoplastic material, preferrably in the case of medical usage of a material which is heat resistant and sterilizable and typically a polymeric plastic material which may be mold injected. One such material is polytrifluoroethylene, available as KEL-F, a registered trademark of 3-M Company.

The coupling is shown with the interconnecting first and second connector bodies in position about to be joined together. The first connector body, generally identified at 11, consists of a central male tube-shaped member 12 which is provided with grooves extending around the longitudinal end of the member 12 to form slots for "O" rings 13. These "O" rings act when the connector bodies are joined together to provide a liquid-tight seal therebetween. Tubular member 12 extends within body 14 to provide a free end 15 which is adapted to be joined to plastic flexible tubing 26 as is illustrated in FIG. 3. Body 14 has extending therefrom in parallel arrangement to the male tube member 12 a pair of enclosing arm members 16. Arm members 16 extend in parallel arrangement to tubular member 12 beyond the end thereof at which point they flare outwardly at an acute angle with respect to the longitudinal axis of the connector assembly as can be seen in the figures to provide oppositely positioned flared segments 17. The function of these flared segments 17 will be described below. At the general region of the arms 16 where the flaring occurs, there are inwardly oriented extensions which project inwardly toward the axis of member 12 to form a pair of flange members 18. Members 18 are shaped to form segments of an arc at their innermost projecting edges and preferably include chamfered curved surfaces 19.

At least the flare segments of the arms are resilient, either due to their size or the nature of the material of which they are composed, so that they may be resiliently urged outwardly from body 11.

The second connector body is generally designated at 20 and consists of a female tubular member 28 having an internal bore of a size to slip over male member 12 and to bear against the "O" rings 13 for sealing. Body 20 has a recessed collar member 21 spaced rearwardly of the open end 27 at a position such that it can latch with the inwardly projecting flanges 18 when the male and female members are joined by slipping tubular female member 20 over tubular member 12. Rearwardly of recessed collar member 21 and projecting outwardly at opposite sides of body 20 are wing members 22 which are spaced and of a size to bear against the internal surfaces of flared members 17 when body 20 is rotated following insertion between flanges 18. These members 22 are of sufficient length to spread members 17 of the resilient collar member assembly 14 so as to separate the flanges 18 and disengage them from recessed collar 21.

In operation, bodies 11 and 20 are joined through the motions illustrated in FIGS. 1 and 2. The operator may lock body 20 at an angle to the axis of body 11 and press female member 28 against the chamfered surface 19 of the flanges 18. This pressure causes the arms 16 to spread (FIG. 3) slightly allowing the entire front portion of female member 28 to slip between flanges 18 and to be slid over male member 12. Body 20 is then pressed inwardly until the spring action or resiliency of arms 16 causes flanges 18 to drop into recessed collar member 21 locking the assembly together as shown in FIG. 4. In order to insure a strong positive lock, the female member is rotated so that members 22 are at some angle other than directly in engagement with flare members 17. To achieve disconnect, body 20 is rotated until members 22 are urged between and pressed against the flared portions 17 to spread arms 16 and flanges 18 outwardly thereby permitting a ready disconnect of member 11 from member 20. This is best seen in FIG. 5. In actual practice, the resiliency of arms 16 acting against wings 22 urges body 20 away of male member 11 thus moving recessed colar 21 away from flanges 18, to assure convenient disengagement. It can thus be seen that both a ready connect and disconnect is provided without further manipulation then has been described above.

What is claimed is:

1. A flow-through connector assembly for use in transmitting the flow of blood and other fluids, comprising in combination:
    a. first and second connector bodies adapted to be couplingly connected together and to be readily disconnected by relative rotation of at least one of said bodies about the body axis and the separation of the two bodies;
    b. the connector bodies each being characterized by a coaxial fluid passageway therethrough with each body having one end thereof adapted to be joined to a fluid conduit and an opposite end adapted for mutual connection with the other connector body to form a continuous fluid passageway therethrough when the bodies are connected together;

c. the said opposite end of one of the connector bodies including a male tubular member and the said opposite end of the other connector body including a female tubular member for receiving the male member upon connecting the two connector bodies together, each of the tubular members comprising a portion of the fluid passageway;

d. a pair of resilient arm members formed integrally with the first connector body and positioned along opposite sides of the tubular member on the first connector body and extending parallel thereto beyond the end of the tubular member at which point each arm has a flared segment which flares outwardly at an acute angle with respect to the longitudinal axis of the connector body and which is of a length approximating the length of said arm, and an inwardly extending flange member carried by each arm at a position beyond the end of the tubular member for receiving the tubular member carried by the second connector body when the two connector bodies are being connected together, the distance between the inward ends of the flanges being less than the outside diameter of the tubular member carried by the second connector body whereby the arms are resiliently spread apart when the tubular member is received between the flanges; and, e. The second connector body being further characterized by an annular recessed collar positioned inwardly of the tubular member carried thereby for receiving the flanges of the first connector body when the tubular members are joined thereby connecting the connector bodies together, and a pair of oppositely positioned members formed integrally with and extending outwardly from the sides of the second connector body from an inward position beyond the recessed collar and the tubular member, the outwardly extending members being of such a length as to bear against the flaring arms when the connected connector bodies are rotated relative to each other whereby the flanges are lifted out of the recessed collar and the connector bodies may be disconnected by separating them.

2. The connector assembly according to claim 1 wherein the connector bodies are composed of a polymeric material.

3. The connector assembly according to claim 2 wherein the bodies are molded.

4. The connector assembly according to claim 2 wherein the material is heat sterilizable.

5. The connector assembly according to claim 1 wherein the tubular member of the first connector body is the male tubular member.

6. The connector assembly according to claim 5 wherein the male member carries at least one "O" ring on its exterior for forming a liquid-tight seal between the male and female members.

7. The connector assembly according to claim 6 wherein two spaced "O" rings are carried by the male member.

8. The connector assembly according to claim 1 wherein the inward ends of the flanges are arcuate.

9. The connector assembly according to claim 8 wherein the arcuate inward ends of te flanges are chamfered.

* * * * *